United States Patent [19]

Heston

[11] Patent Number: 4,925,835
[45] Date of Patent: May 15, 1990

[54] AZIRIDINYL PUTRESCINE CONTAINING COMPOSITIONS AND THEIR USES IN TREATING PROSTATE CANCER

[75] Inventor: Warren D. W. Heston, Montrose, N.Y.

[73] Assignee: Sloan-Kettering Institute for Cancer Research, New York, N.Y.

[21] Appl. No.: 113,550

Related U.S. Application Data

[63] Continuation-in-part of Ser. No. 858,348, May 1, 1986, abandoned, which is a continuation of Ser. No. 700, 644, Feb. 12, 1984, abandoned.

[22] Filed: Oct. 26, 1987

[51] Int. Cl.$^5$ .............................................. A61K 31/33
[52] U.S. Cl. ..................................................... 514/183
[58] Field of Search ......................... 514/183; 424/244

[56] References Cited

U.S. PATENT DOCUMENTS

| | | | |
|---|---|---|---|
| 3,487,157 | 12/1969 | Pierce | 514/183 |
| 4,267,174 | 5/1981 | Berger et al. | 514/183 |
| 4,321,194 | 3/1982 | Bosies et al. | 514/183 |
| 4,370,323 | 1/1983 | Kampe et al. | 514/183 |
| 4,517,183 | 5/1985 | Bosies et al. | 514/183 |
| 4,686,215 | 8/1987 | Kalvinsh et al. | 514/183 |
| 4,704,384 | 11/1987 | Driscoll et al. | 514/183 |

FOREIGN PATENT DOCUMENTS

47-13499 4/1972 Japan .................................. 514/183

OTHER PUBLICATIONS

Chemical Abstracts, 74:77493y, (1971).
Chemical Abstracts, vol. 74, p. 196F, (1971).

Primary Examiner—Jacqueline V. Howard
Assistant Examiner—Margaret B. Medley
Attorney, Agent, or Firm—John P. White

[57] ABSTRACT

This invention relates to methods of inhibiting the proliferation of prostate cancer cells comprising contacting the cells with an effective amount of a cytotoxic polyamine compound.

The invention also relates to methods of inhibiting the proliferation of prostate cancer cells in a subject afflicted with prostate cancer.

The invention further concerns therapeutic compositions comprising an effective prostate cancer cell proliferation inhibiting amount of 1-(4-aminobutyl) aziridine and a pharmaceutically acceptable carrier.

The invention also concerns two-component therapeutic compositions.

29 Claims, 4 Drawing Sheets

AZIRIDINYL PUTRESCINE CONTAINING COMPOSITIONS AND THEIR USES IN TREATING PROSTATE CANCER

The invention described herein was made in the course of work under Grant No. CA 39203 from the National Institute of Cancer, U.S. Department of Health and Human Services. The U.S. Government has certain rights in this invention.

This application is a continuation-in-part of U.S. application Ser. No. 858,348, filed May 1, 1986, which is a continuation of U.S. application Ser. No. 700,644, filed Feb. 12, 1984, both now abandoned.

BACKGROUND OF THE INVENTION

Throughout this application various publications are referenced and citations provided for them. The disclosure of these publications in their entireties are hereby incorporated by reference into this application to more fully describe the state of the art to which this invention pertains.

Putrescine, also known as 1,4-butanediamine, is a normal nontoxic constituent of mammalian cells. Putrescine is formed via the decarboxylation of ornithine. The rate limiting enzyme in the synthesis of putrescine and other polyamines is ornithine decarboxylase. In rat prostate cells, ornithine decarboxylase activity is quite sensitive to in vivo inhibition by the polyamine depleting agent, difluoromethylornithine. In vitro inhibition by the polyamine depleting agent, difluoromethylornithine shows that depletion of polyamines caused by the addition of difluoromethylornithine enhances the uptake of exogenously added polyamines. Pretreatment with difluoromethylornithine in vivo significantly increases the uptake of radioactive putrescine by prostate cancer cells. Kadmon, et al., J. Nucl. Med., 23: 998-1002, No. 11 (November 1982).

Following treatment with the polyamine-depleting agent, difluoromethylornithine, putrescine and cadaverine, another polyamine, are taken up by prostate derived tumors much more readily than other polyamines. Heston, et al., Cancer Res. 44: 1034-1040 (1984).

The invention described herein relates to the use of putrescine-derived cytotoxic polyamines compounds as proliferation inhibitors of human prostatic cancer cells.

The invention described herein further relates to the use of polyamine-depleting agents to facilitate the uptake of cytotoxic polyamine compounds by human prostatic cancer cells.

SUMMARY OF THE INVENTION

The present invention provides a method of inhibiting the proliferation of prostate cancer cells comprising contacting the cells with an effective proliferation inhibiting amount of a cytotoxic polyamine compound.

Additionally, the present invention provides a method for inhibiting the proliferation of prostate cancer cells in a subject afflicted with prostate cancer comprising administering to the subject an effective proliferation inhibiting amount of a cytotoxic polyamine compound.

The invention also concerns a therapeutic composition comprising an effective prostate cancer cell proliferation inhibiting amount of 1-(4-aminobutyl) aziridine and a phamaceutically acceptable carrier.

Another embodiment of this invention concerns a two component therapeutic composition which comprises separate first and second components, the first component comprising an effective prostate cancer cell proliferation inhibiting amount of a cytotoxic polyamine compound and the second component comprising an effective depleting amount of polyamine depleting agent.

DETAILED DESCRIPTION OF THE INVENTION

Figure 1:
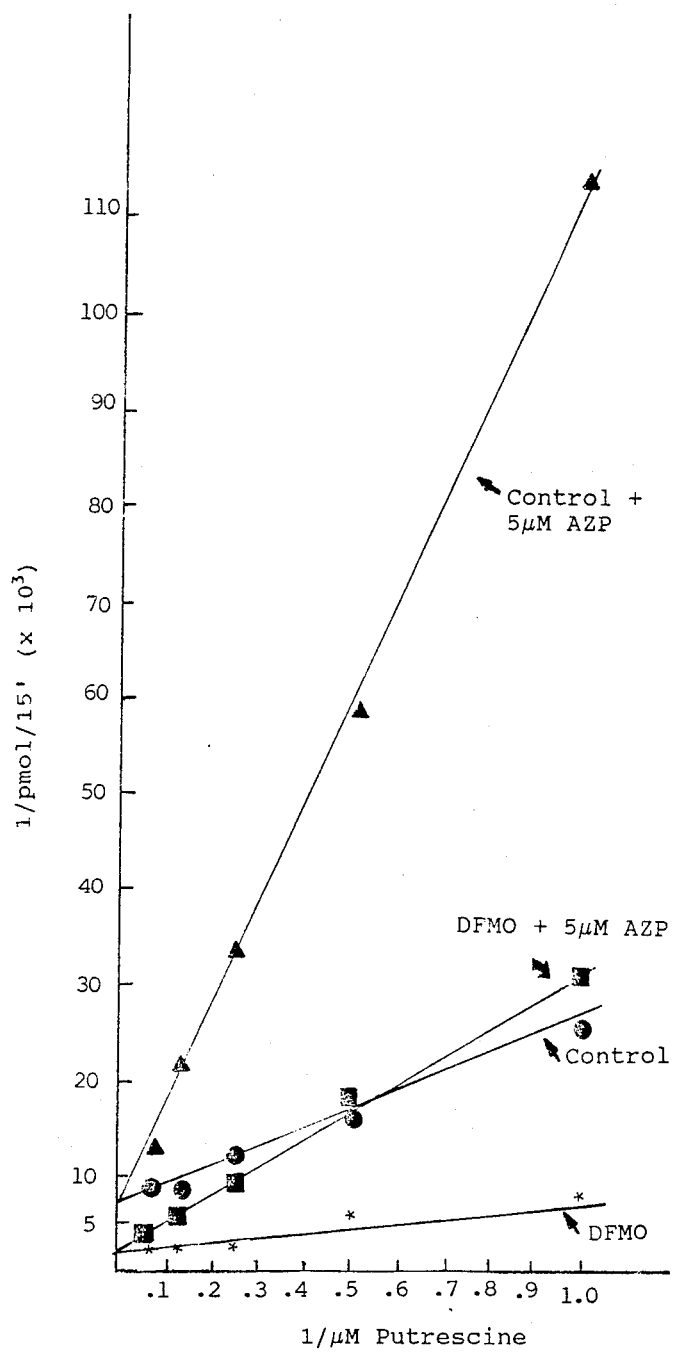
FIG. 1. Lineweaver-Burk plot of the uptake of [$^{14}$C]putrescine by DFMO-pretreated cells. The ordinate is expressed as 1/pmol/15 min. The abscissa is expressed as 1 $\mu$M concentrations containing from 16 to 1.0 $\mu$M [$^{14}$C]putrescine.

This invention provides a method of inhibiting the proliferation of prostate cancer cells comprising contacting the cells with an effective proliferation-inhibiting amount of a cytotoxic polyamine compound. As used herein cytotoxic polyamine compounds include 1-(4-aminobutyl) aziridine, also known as aziridinyl putrescine or AZP, ($N^1$-3-aminopropyl)-1,4-butanediamine) aziridine, also known as aziridinyl spermidine, and (N,$N^1$-1-bis(3-aminopropyl)-1,4-(butanediamine) aziridine also known as aziridinyl spermine. An example of a cytoxic polyamine compounds useful in practice of this invention includes 1-(4-aminobutyl) aziridine.

In one embodiment of the invention where the cytotoxic polyamine compound comprises 1-(4-aminobutyl) aziridine, the method of inhibiting the proliferation of prostate cancer cells additionally comprises contacting the cells with an effective depleting amount of a polyamine depleting agent. As used herein, polyamine depleting agents include difluoromethylornithine, also known as DFMO and (2R,5R)-6-heptyne-2,5-diamine also known as R,R-MAP or R,R-methylacetylinic putrescine. An example of a polyamine depleting agent useful in the practice of this invention is difluoromethylornithine.

Another aspect of the invention provides a method for inhibiting the proliferation of prostate cancer cells in a subject afflicted with prostate cancer comprising administering to the subject, such as a human patient, an effective proliferation inhibiting amount of a cytotoxic polyamine compound.

The cytotoxic polyamine compound, e.g., 1-(4-aminobutyl) aziridine or ($N^1$-(3 aminopropyl)-1,4-butanediamine) aziridine or (N,$N^1$-bis(3-aminopropyl)-1,4-butanediamine) aziridine may be administered by any of a variety of well-known administration routes including intratumorally, intravenously, intraarterially, subcutaneously, intramuscularly or intraperitoneally. Oral administration is not recommended because these polyamine compounds tend to be unstable at acidic pHs such as are in the mouth. If given orally, these compounds will also break down in the low pH in the stomach and lose activity.

In embodiments where the cytotoxic polyamine compound comprises 1-(4-aminobutyl) aziridine, the above-described method of inhibiting the proliferation of prostate cancer cells in a subject additionally comprises administering to the subject an effective depleting amount of a polyamine depleting agent. An example of a polyamine depleting agent useful in this invention is difluoromethylornithine.

The polyamine depleting agent may be administered in a variety of routes, including intratumorally, intravenously, intraarterially, subcutaneously, intramuscularly, intraperitoneally, or orally. It is desirable that the cytotoxic polyamine compound and the polyamine depleting agent be separately administered due to the latter's potential to act also as an alkylating agent which will reduce the inhibiting effectiveness of the polyamine compound.

The polyamine depleting agent, e.g., difluoromethylornithine or (2R,5R)-6-heptyne-2,5 diamine, should be administered before the cytotoxic polyamine compound, e.g., 1-(4-aminobutyl) aziridine, is administered to the subject.

The concentration or amounts of the cytotoxic polyamine compounds and polyamine depleting agents administered will vary widely depending upon the severity of the treatment, the condition of the subject being treated, and the particular compound or agent being employed.

Effective proliferation inhibiting amounts of the cytotoxic polyamine compound will vary widely in a range from about 0.5 uM to about 50 mM, preferably from about 1.0 uM to about 25 mM. For example, when contacting prostate cancer cells in culture, it has been found by this invention that an effective amount of 1-(4-aminobutyl) aziridine may range from 1.0 uM to about 25 uM. 50 uM 1-(4-aminobutyl) aziridine has been found to inhibit in vitro prostate cancer cells by approximately 64%. When employed therapeutically in a subject, such as a rat, an effective amount of 1-(4-aminobutyl) aziridine may range from about 0.1 mg/kg/day to as much as 5 mg/kg/day. 2 mg/kg/day 1-(4-aminobutyl) aziridine administered to Copenhagen rats over a fourteen day period has been found to reduce the size of the normal ventral prostate by approximately 67%.

Effective depleting amounts of the amine depleting agent may vary widely in a range of from about 1.0 uM to about 1.0 mM, preferably from about 250 uM to about 0.5 mM.

This invention also concerns a therapeutic composition comprising an effective prostate cancer cell proliferation inhibiting amount of 1-(4-aminobutyl) aziridine and a pharmaceutically acceptable carrier.

In the embodiments, the effective amounts of 1-(4-aminobutyl) aziridine in the therapeutic composition will vary as above described, i.e., from about 0.5 uM to about 50 mM, preferably from about 1.0 uM to about 25 mM.

This invention also concerns a two component therapeutic composition which comprises separate first and second components, the first component comprising an effective prostate cancer cell proliferation inhibiting amount of a cytotoxic polyamine compound and the second component comprising an effective depleting amount of an polyamine depleting agent. An example of a cytotoxic polyamine compound useful in the two component therapeutic composition of this invention is 1-(4-aminobutyl) aziridine. An example of a useful polyamine depleting agent in the above described composition is difluoromethylornithine. Effective amounts of the cytotoxic polyamine compound, e.g. 1-(4-aminobutyl) aziridine, may range from about 0.5 uM to about 50 mM, preferably from about 1.0 uM to about 25 mM. Effective amounts of the polyamine depleting agent, e.g., difluoromethylornithine, may range from about 0.5 uM to about 50 mM, preferably from 1.0 uM to about 25 mM.

This invention is illustrated in the Experimental Detail and Discussion Section which follows. This section is set forth to aid in an understanding of the invention but is not intended to, and should not be construed to, limit in any way the invention as set forth in the claims which follow thereafter.

EXPERIMENTAL DETAILS AND DISCUSSION

Effect of 1-(4-aminobutyl) aziridine on human prostate cancer PC-3 cells:

Aziridinyl putrescine 1-(4-aminobutyl) aziridine was synthesized using the method as described by Piper, et al., J. Med. Chem. 12: 236–243 (1968). Cells of the human prostate cancer cell line PC-3 were used.

$10^3$ PC-3 human cells were plated in RPMI 1640 with 10% FCS/3 ml in 60 mm² petri dishes. The cell plates were incubated either with, or without difluoromethylornithine for 48 hours. This was followed by aspiration, and replacement with a medium containing either no additives, 50 uM 1-(4-aminobutyl) aziridine, 1 mM putrescine, or both 50 uM 1-(4-aminobutyl) aziridine and 1 mM putrescine. The media were aspirated after 1 hour, and replaced with a drug free medium. Incubation continued for 5 days.

The results of these experiments follow in Table 1:

TABLE 1

| Effect of Treatment on Human PC-3 Cells | |
|---|---|
| TREATMENT | CLONOGENIC SURVIVORS |
| Control | 584 ± 70* (100%) |
| DFMO | 549 ± 57 (94%) |
| AZP | 210 ± 30 (36%) |
| DFMO + AZP | 5 ± 2 (1%) |
| DFMO + AZP + PUT | 505 ± 76 (86%) |

*Represents mean number of colonies ± one standard deviation of triplicate assay. Number in parenthesis is percent of control.

Table 1 shows that 1-(4-aminobutyl) aziridine, at 50 uM inhibited the proliferation of human prostate cancer cells in culture by 64%. Difluoromethylornithine, alone, had little effect. In combination, 1-(4-aminobutyl) aziridine and difluoromethylornithine inhibited the proliferation of prostate cancer cells i.e., reduced the number of viable cancer cells by 99%.

1-(4-aminobutyl) aziridine is cytotoxic for prostate cancer cells and inhibits their proliferation. Additionally, the combination of 1-(4-aminobutyl) aziridine and difluoromethylornithine produces unexpected results on prostate cancer cells.

Cytotoxic Activity of 1-(4-aminobutyl) aziridine against the PC-3 human prostatic carcinoma cell line:

Materials and Methods

Chemicals

The preparation of 1-(4-aminobutyl) aziridine from 1,4-diaminobutane (putrescine) was performed by the three-step synthetic method reported by Piper et al. supra. Demonstration of the alkylating activity of 1-(4-aminobutyl) aziridine was determined with 4-(p-nitrobenzyl)pyridine as described by Colvin et al., Cancer Res., 36: 1121–1126 (1976).

Merrell Dow Pharmaceuticals, Inc. was the source of difluoromethylornithine Radiolabeled [$^{14}$C]putrescine (113 mCi/mmol) and α-1-[$^{14}$C]carboxy-1-ornithine (58 mCi/mmol) were obtained from Amersham, Arlington Heights, IL. HPLC grade acetonitrile was obtained from Scientific Products. HPLC grade perchloric acid was obtained from GFS Chemical, Columbus, OH, HPLC grade methanol and sodium phosphate and Scintiverse I and Scintilene scintillation cocktails were obtained from Fisher Scientific Co., Fairlawn, NJ. The standards for the polyamine assay and all other standard laboratory chemicals were obtained from Sigma Chemical Co., St. Louis, MO.

Cell Culture.

All tissue culture media and tissue culture media and tissue culture additives, such as RPMI 1640 media, 10% FCS, 100X concentrations of penicillin, streptomycin, glutamine, nonessential amino acids, HBSS, and trypsin-EDTA solutions were obtained from the Media Preparation Facility, Memorial Sloan-Kettering Cancer Center. The human prostatic carcinoma-derived cell line PC-3 was obtained from the American Type Culture Collection, Rockville, MD.

Cell Growth Assay.

Assays of cell growth were performed by plating $3 \times 10^4$ PC-3 cells in RPMI 1640 medium with 10% FCS and allowing them to attach overnight. The following morning the medium was replaced with incubation medium consisting of RPMI 1640, 10% FCS, 100 μM aminoguanidine, 100 units/ml of penicillin, 100 μg/ml of streptomycin, and 2 mM glutamine, with or without 1 mM difluoromethylornithine. Two days later the medium was aspirated and replaced with or without 1-(4-aminobutyl) aziridine at the designated concentration usually for 1 h or for the designated length of time. Following the 1-h incubation, the medium of all groups was aspirated and the dishes were rinsed with HBSS and replaced with fresh incubation medium. Either daily or 8 days following plating, the Petri dishes were rinsed with HBSS and the cells were lifted from the plate by trypsinization. The dishes were examined for completeness of cell removal by examination with an inverted microscope. The cells were counted with a Zeiss microscope using a hemocytometer. Tumor cell population doubling time was determined by ploting the natural logarithm (ln) of the number of cells versus the days following plating. The slope of this line was determined using the Memorial Sloan-Kettering Cancer Center Clin computer system statistical analysis package. Doubling time (DT) was determined as ln 2/slope=DT. Statistical differences in cell number between groups were determined by Student's t statistic with the aid of the Memorial Sloan-Kettering Cancer Center Clin computer using the statistics program.

Polyamine Uptake.

Fifty thousand PC-3 cells were plated in 12-well plates and 18 h later the incubation medium was removed and replaced with 1 ml or RPMI 1640 medium containing 25 mM 4-(2-hydroxyethyl)-1-piperazineethansulfonic acid buffer, 100 μM aminoguanidine, and 10% FCS. Forty-eight h later the medium was replaced with medium which contained [$^{14}$C]putrescine in concentrations ranging from 16 to 1.0 μM with or without 5 1M 1-(4-aminobutyl) aziridine. Following incubation at 37° C. for 15 min the [$^{14}$C]putrescine-containing medium was aspirated, and the cells were rinsed rapidly 4 times with HBSS. Following the last rinse, 1.0 ml of a solution of 0.1N NaOH was added and after a 2-h incubation at room temperature a 0.2-ml aliquot was added to 1 ml of 2% glacial acidic acid and 10 ml of Scintiverse 1 scintillation cocktail and the radioactive disintegrations were determined with a Packard Tri-Carb 300 scintillation spectrophotometer. Counting efficiency for $^{14}$C was 80%. Kinetic analysis of uptake was performed by graphic methods as described by Dixon and Webb, Enzymes, p. 322, New York Academic Press (1959).

Polyamine Assays.

One million PC-3 cells were plated in sextuplicate in 60-min² Petri dishes and the following morning their incubation medium was changed and replaced with medium which contained or did not contain 1 mM difluoromethylornithine. Forty-eight h later the medium was removed and replaced with medium which did or did not contain 25 μM 1-(4-aminobutyl) aziridine. One h later the medium was aspirated and the cells were rinsed with cold HBSS. Three plates were treated with dilute trypsin to release the cells from the plate and provide a single cell suspension. The viability of the cells and the number of cells per plate were determined by trypan blue exclusion and counting with the aid of a hemocytometer. The other three plates were extracted with aid of a hemocytometer. The other three plates were extracted with 0.4N perchloric acid and the polyamines were measured by fluorescence following postcolumn derivatization with o-phthalaldehyde following separation by the reverse phase ion-pair high performance liquid chromatography procedure of Wagner et al., J. Chomatogr., 227: 349–368, 1982.

RESULTS

In FIG. 1 a Lineweaver-Burk plot of the uptake of [$^{14}$C]-putrescine into the PC-3 cells is presented and was used to determine the $K_m$ (intercept x axis) and $V_{max}$ (intercept y axis) for putrescine. Plots of 1-(4-aminobutyl azirdine produced changes in uptake that were consistent with competitive inhibition. The apparent $K_i$ for 1-(4-aminobutyl) aziridine was calculated using the equation:

The $K_m$ for putrescine was calculated to be 2.5 $\mu$M with or without difluoromethylornithine pretreatment and the $V_{max}$ of 40 pmol/15 min/$10^5$ cells without difluoromethylornithine pretreatment and 190 pmol/15 min/$10^5$ cells following difluoromethylornithine pretreatment. The apparent $K_i$ for 1-(4-aminobutyl) aziridine was calculated to be 1 $\mu$M with or without difluoromethylornithine pretreatment.

Figure 2:
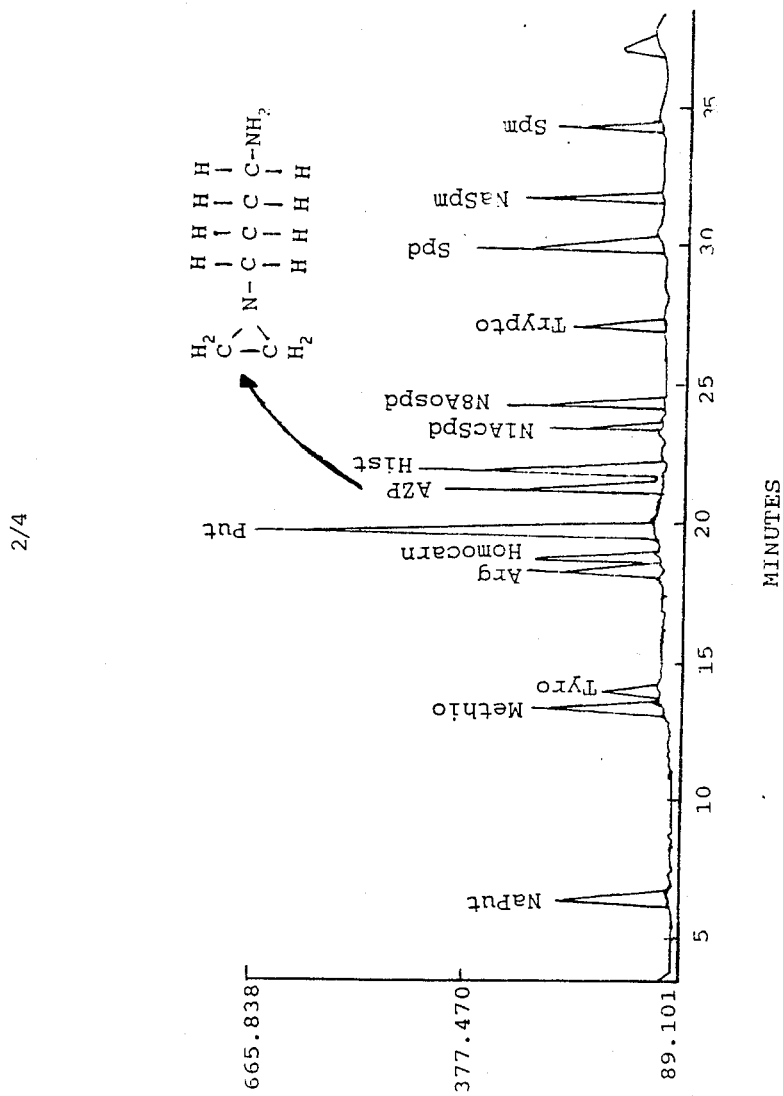
FIG. 2. Chromatogram of AZP with standards used in polyamine assay with relative fluorescence units and time from sample injection plotted on the ordinate and abscissa, respectively. Abbreviations, retention times, and concentrations are: Put, putrescine, 19.61 min, 157 pmol; AZP, 21.15 min, 100 pmol; Hist, histamine, 21.82 pmol; Spd, spermidine, 29.9 min, 83 pmol; NaSpm, acetylspermine, 31.7 min, 50 pmol; Spm, spermine, 34.26 min, 60 pmol.

1-(4-aminobutyl) aziridine (100 nmol) produced an absorbance increase of 0.7 with 4-(p-nitrobenzyl)pyridine in 5.0 ml when incubated in 0.1M acetate, PH 4.5, at 37° C. for 2 h. This demonstrated that 1-(4-aminobutyl) aziridine has alkylating activity. As shown in FIG. 2, when 1-(4-aminobutyl) aziridine was injected with polyamine standards for chromatographic separation using HPLC a single discrete peak eluting between putrescine and histamine was observed. The retention times were: putrescine, 19.6 min; 1-(4-aminobutyl) aziridine, 21.1 min; and histamine, 21.8 min.

In Table 2 are listed the values for the triplicate assays of the concentrations of polyamine observed in nontreated cells, cells treated with 1-(4-aminobutyl) aziridine for 1 h, cells pretreated for 48 h with 1 mM difluoromethylornithine and then incubated in drug free medium for 1 h, or cells pretreated for 48 h with difluoromethylornithine, rinsed free of difluoromethylornithine, and then incubated with 25 $\mu$M 1-(4-aminobutyl) aziridine for 1 h. All groups had cell viabilities greater than 95% and cell numbers were 4.9±0.6 (SE), 4.9±0.7, 4.8±0.4, and 4.6±0.4×$10^6$ cells for the control, 1-(4-aminobutyl) aziridine, difluoromethylornithine, and difluoromethylornithine+1-(4-aminobutyl) aziridine groups, respectively. The apparent amount of 1-(4-aminobutyl) aziridine in the difluoromethylornithine-treated cells was 3.7 times that of the 1-(4-aminobutyl) aziridine-only-treated cells. No $N^8$-acetylspermidine, acetylputrescine, or cadaverine was detected in any group. A peak was detected at a wavelength of 254 nm in the difluoromethylornithine treatment groups that corresponds to the retention time of decarboxylated S-adenosylmethionine. It was not observed in the groups that did not receive difluoromethylornithine, and its concentration did not change significantly with 1-(4-aminobutyl) aziridine treatment.

TABLE 2
CYTOTOXIC ACTIVITY OF AZIRIDINYLPUTRESCINE
Intracellular polyamine levels of control and DFMO pretreated PC-3 cells following 1-h incubation of AZP

| Treatment[a] | Polyamine levels[b] | | | (pmol/$10^6$) | | |
|---|---|---|---|---|---|---|
| | PUT[c] | AZP | Hist | Spd | NaSpm | Spm |
| Control | 2459 ± 137 | | 98 ± 10 | 2717 ± 66 | 108 ± 21 | 3382 ± 193 |
| DFMO only | 192 ± 34 | | 98 ± 26 | 171 ± 66 | 130 ± 10 | 3046 ± 554 |
| AZP only | 2520 ± 170 | 115 ± 32 | 86 ± 25 | 2884 ± 100 | 125 ± 28 | 3604 ± 323 |
| DFMO + AZP | 281 ± 73 | 425 ± 29 | 75 ± 17 | 144 ± 32 | 111 ± 27 | 3431 ± 290 |

[a]PC-3 cells were incubated with or without 1 mM DFMO for 48 h. Cells were then rinsed free of DFMO and incubated for 1 h with 25 $\mu$M AZP. The cells were washed free of AZP by three rinses of HBSS. With one set of triplicate plates, the cells were resuspended and counted by hemocytometer and viability was determined by trypan dye exclusion (viability > 95%). Another set triplicate plates was extracted with ice-cold perchloric acid and filtered and the polyamineconcentrations were determined by HPLC.
[b]Mean ± SE for a triplicate assay. Histamine is included as a nonpolyamine control.
[c]Put, putrescine; Hist, histamine; Spd, spermidine; NaSPM, N-acetylspermine; Spm, spermine.

Figure 3:
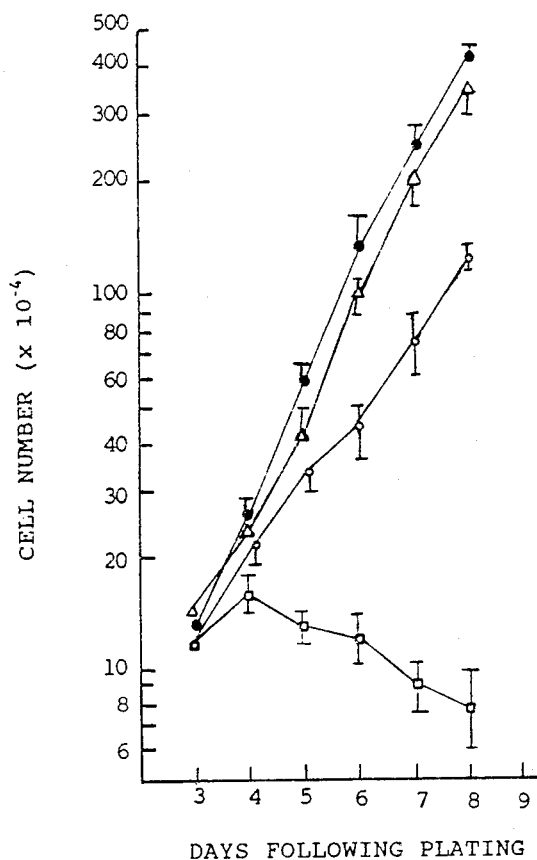
FIG. 3. Effect of AZP on the growth of PC-3 cells with or without DFMO pretreatment. PC-3 cells ($3 \times 10^4$) were plated in 60-mm$^2$ Petri dish in RPMI 1640-10% FCS and allowed to attach overnight. The following day the medium was aspirated and replaced with RPMI 1640, 10% FCS, 100 $\mu$M aminoguanidine with or without 1 mm DFMO. Forty-eight h later the medium was aspirated, the dishes were rinsed once with HBSS, and the cells were incubated with RPMI 1640-10% FCS-100 $\mu$M aminoguanidine with or without 25 $\mu$M AZP for 1 h. Following the 1-h incubation the medium was aspirated, the plates were rinsed twice with HBSS, and the incubation was continued with fresh RPMI 1640-10% FCS-100 $\mu$M aminoguanidine. At the indicated times following initial plating the cells were lifted from the plate by trypsinization and were examined for their ability to exclude trypan blue. Total cell counts were obtained with the aid of a hemocytometer, and the completeness of the removal of the cells from the dish was verified by the examination of each dish with the inverted microscope. ●, control; △, DFMO; ○, AZP; □, DFMO+AZP. Points, means; bars, SE.

FIG. 3 illustrates the effects of 25 $\mu$M 1-(4-aminobutyl) aziridine treatment alone or following 48-h 1 mM difluoromethylornithine pretreatment on the growth of the PC-3 cells as observed daily following a 1-h incubation with 1-(4-aminobutyl) aziridine. The doubling time (days) for the groups were: control, 1.08±0.05; difluoromethylornithine, 1.14±0.05; and 1-(4-aminobutyl) aziridine, 1.53±0.06 (mean±SE). After the day following treatment the difluoromethylornithine/1-(4-aminobutyl) aziridine group decreased in cell number. On the day of plating (day 0) 3×$10^4$ PC-3 cells per dish were plated. On day 8 following plating there were 414±17, 340±54, 123±10, and 7.4±2.5×$10^4$ cells per dish in the control, difluoromethylornithine, 1-(4-aminobutyl) aziridine, and difluoromethylornithine/1-(4-aminobutyl) aziridine dishes, respectively (mean±SD of triplicates). The numbers of cells recovered from the 1-(4-aminobutyl) aziridine and difluoromethylornithine/1-(4-aminobutyl) aziridine groups differed significantly from all other groups (P<1-(4-aminobutyl) aziridine groups differed significantly from all other groups (P<0.05) while the DFMO and control groups did not differ significantly from each other (P<0.05).

Figure 4:
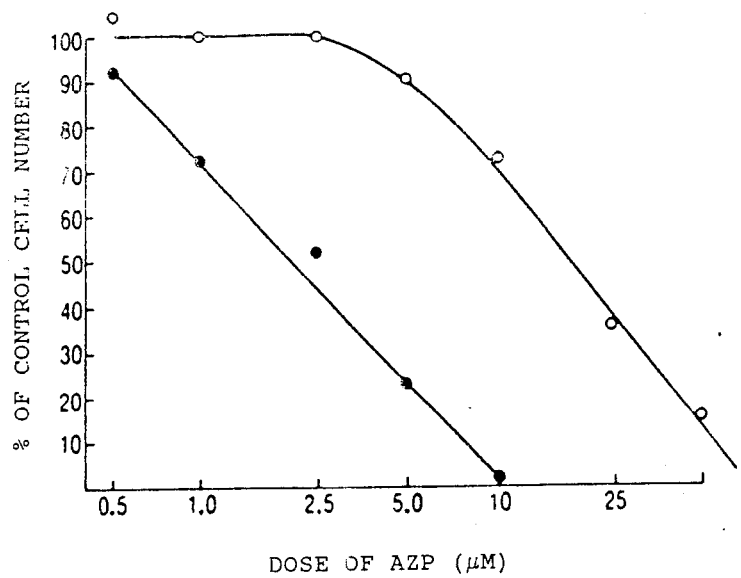
FIG. 4. Dose-effect relationship of AZP on the growth on PC-3 prostatic cancer cells. PC-3 cells ($3 \times 10^4$) were plated in RPMI 1640-10% FCS in 60-mm$^2$ Petri dishes and allowed to attach overnight. The following day the medium was aspirated and replaced with RPMI 1640-10% FCS-100 $\mu$M aminoguanidine with or without 1 mm DFMO. Forty-eight h later the medium was aspirated, and the cells were rinsed once with HBSS and replaced with RPMI 1640-10% FCS-100 $\mu$M aminoguanidine with or without the indicated $\mu$M concentrations of AZP. After a 1-h incubation the medium was aspirated, the cells were rinsed twice with HBSS, and the incubation was continued with fresh RPMI 1640-10% FCS-100 $\mu$M aminoguanidine. Eight days following plating the cells were lifted from the plates by trypsinization and were counted with the aid of a hemocytometer and expressed as a percentage of control (100% without DFMO, $212 \pm 31 \times 10^4$; 100% with DFMO pretreatment, $219 \pm 25 \times 10^4$ cells, respectively). ●, DFMO pretreated; ○, without DFMO.

FIG. 4 demonstrates the effect of the exposure of PC-3 cells to different concentrations of 1-(4-aminobutyl) aziridine for 1 h. The 50% effective dose for 1-(4-aminobutyl) aziridine was decreased from 18 $\mu$M to 2.1 $\mu$M by difluoromethylornithine pretreatment. The effect of exposing the cells to a single concentration of 1-(4-aminobutyl) aziridine for an increasing length of time is shown in Table 3. There was increasing toxicity to the cells the longer they were exposed to 1-(4-aminobutyl) aziridine, consistent with a concentration- and time-dependent toxicity. Nearly equivalent reductions of 12 and 9% were observed by 24 h in the nondifluoromethylornithine-treated cells and 8 h in the difluoromethylornithine-pretreated cells.

TABLE 3

Effect of increasing duration of exposure to AZP on PC-3 cell growth

| Incubation (h)[a] | Cell no. × $10^{-4}$ | |
|---|---|---|
| | Control | DFMO pre-treated |
| 0 | 241 ± 11(100%)[b] | 220 ± 11(100%) |
| 1 | 236 ± 8(98%) | 161 ± 13(73%) |
| 2 | 202 ± 11(84%) | 114 ± 10(52%) |
| 4 | 158 ± 20(66%) | 70 ± 8(32%) |
| 8 | 122 ± 16(51%) | 19 ± 7(9%) |
| 24 | 30 ± 11(12%) | 2 ± 1(0.9%) |

[a] Thirty thousand PC-3 cells were plated in 60-mm² Petri dishes in RPMI 1640-10% FCS. The next day the medium was aspirated and replaced with RPMI 1640-10% FCS medium with 100 μM aminoguanidine with or without 1 mM DFMO. Forty-eight h later the medium was aspirated. The cells were rinsed and incubated with RPMI 1640-10% FCS with 100 μM aminoguanidine with no additions or with 1 μM AZP for various lengths of time. Following the respective incubation period the cells were rinsed twice with HBSS and the incubation was continued with fresh medium. Eight days following the initial plating the dishes were rinsed with HBSS and the cells were lifted from the dishes by trypsinization and counted by hemocytometer.
[b] Mean ± SE. Numbers in parentheses, cell number as a percentage of the control mean cell number.

Putrescine can reverse the growth-inhibitory activity of 1-(4-aminobutyl) aziridine as is shown in Table 4. Treatment of PC-3 cells for 1 h with 10 μM concentration did not significantly alter the number of cells obtained. When 1-(4-aminobutyl) aziridine and putrescine were simultaneously incubated with the cells for 1 h there was restoration of cell growth to 87% of that of the untreated control. If putrescine was incubated with the cells before 1-(4-aminobutyl) aziridine, there was some restoration of cell growth but not nearly as complete as that seen when the cells were incubated with putrescine within 6 h following incubation with 1-(4-aminobutyl) aziridine. By 24 h following incubation with 1-(4-aminobutyl) aziridine, incubation with putrescine could no longer reverse the growth-inhibitory activity of 1-(4-aminobutyl) aziridine.

TABLE 4

Putrescine reversal of aziridinylputrescine cytotoxicity[a]

| Treatment group | Cell no.[b] × $10^{-4}$ |
|---|---|
| None | 410 ± 39(100%) |
| Put,[c] 100 μM | 438 ± 16(106%) |
| AZP, 10 μM | 39 ± 10(9%) |
| AZP and Put | 357 ± 64(87%) |
| Put(0), AZP | 86 ± 13(21%) |
| AZP (0), Put | 335 ± 57(82%) |
| AZP (2), Put | 360 ± 51(88%) |
| AZP (5), Put | 259 ± 28(63%) |
| AZP (23), Put | 54 ± 12(13%) |

[a] Thirty thousand PC-3 cells were plated in 60-mm² Petri dishes in RPMI 1640-10% FCS. The next day the medium was aspirated and replaced with RPMI 1640-10% FCS containing 100 μM aminoguanidine and 1 mM DFMO. Forty-eight h later the medium was aspirated, the cells were rinsed with HBSS and exposed for 1 h to either AZP or Put or both, either simultaneously or following each other as designated with the intervening time interval in hours defined in parentheses between the compounds. Following the 1-h incubation of the cells with the agent the medium containing the agent was removed, the cells were rinsed twice with HBSS, fresh RPMI 1640-10% FCS-100 mM aminoguanidine containing medium was added, and the incubation at 37° C. was continued. Eight days following plating the dishes were rinsed with HBSS and the cells were removed from the dish by trypsinization. The completeness of the removal of cells from the dish was verified by examination with an inverted microscope. The cells were enumerated with the aid of a hemocytometer.
[b] Mean ± SE. Numbers in parentheses, mean number as a percentage of control.
[c] PUT, putrescine.

DISCUSSION 1-(4-aminobutyl) aziridine was similar to putrescine in that it competitively inhibited the uptake of putrescine into PC-3 cells. Neither the competitive nature nor the $K_i$ of this inhibition was changed with difluoromethylornithine pretreatment in keeping with the finding that the observed $K_m$ for putrescine uptake was not altered by difluoromethylornithine pretreatment. Difluoromethylornithine pretreatment increased the $V_{max}$ for putrescine uptake and the extent of uptake of aziridinylputrescine. In terms of polyamine transport, aziridinylputrescine behaved in a similar fashion to that of putrescine. However, putrescine exhibited no growth-inhibitory activity toward PC-3 cells while aziridinylputrescine was definitely growth inhibitory even following a brief 1-h exposure to the cells.

In vivo effect of 1-(4-aminobutyl) aziridine on rat prostrate 1-(4-aminobutyl) aziridine, difluoromethylornithine, and a combination of 1-(4-aminobutyl) aziridine and difluoromethylornithine were tested in vivo for antiprostatic activity using Copenhagen rats. The normal rat prostate is often used as a model or control for drugs which are suspected of having antiprostatic cancer activity. Sloan, et al., Cancer Chemother. Rep. 59: 185-194 (1975). 1-(4-aminobutyl) aziridine, difluoromethylornithine, and a combination of 1-(4-aminobutyl) aziridine and difluoromethylornithine were administered to twenty-eight (28) Copenhagen rats for 14 days. 1-(4-aminobutyl) aziridine was administered by an infusion mini-pump implanted intraperitoneally.

Difluoromethylornithine was administered orally. The 1-(4-aminobutyl) aziridine was delivered at a rate of 2 mg/kg/day. A similar amount of difluoromethylornithine was administered orally on a daily basis. Before loading the infusion pump, the pH of 1-(4-aminobutyl) aziridine was adjusted to 7.5 with hydrochloric acid. The pump rate was 0.5 u./hr.

The prostates of the twenty-eight (28) subjects were removed, freed of fat and weighed to the nearest milligram. The results of these weighings are set forth in Table 5.

TABLE 5

| TREATMENT | Ventral Prostate | Dorsal Lateral Prostate |
|---|---|---|
| Control (N = 6) | 560 ± 33 | 531 ± 102 |
| AZP (N = 8) | 378 ± 30[1] | 474 ± 39 |
| DFMO (N = 6) | 377 ± 16[1] | 445 ± 32 |
| AZP + DFMO (N = 6) | 243 ± 21[1,2] | 313 ± 27[1] | a - milligram wet weight (SEM)
[1] - p < .05 vs control
[2] - p < .05 vs difluoromethylornithine control The results in Table 5 illustrate that 1-(4-aminobutyl) aziridine treatment significantly decreased the size of the normal ventral prostates, indicating the antiprostatic activity of this compound. At this dosage level, the administration of 1-(4-aminobutyl) aziridine produced no evidence of animal toxicity e.g., weight or fur loss, poor posture. Examination of the animals at the time of sacrifice was also unremarkable in that no other organs, e.g., liver, spleen, intestine, kidneys, demonstrated any evidence of toxicity.

The results in Table 5 also indicate the combination of 1-(4-aminobutyl) aziridine and difluoromethylornithine, produced greater size reduction than that produced by either 1-(4-aminobutyl) aziridine or difluoromethylornithine alone.

What is claimed is:

1. A method of inhibiting the proliferation of a human prostate cancer cells comprising contacting the cells with an amount of a cytotoxic polyamine selected from the group consisting of 1-(4-aminobutyl) aziridine, ($N^1$-(3-aminopropyl)-1,4-butanediamine) aziridine, and (N,$N^1$-bis (3-aminopropyl)-1,4-butanediamine) aziridine, effective to inhibit proliferation of the cells.

2. A method of claim 1, wherein the cytotoxic polyamine compound comprises 1-(4-aminobutyl) aziridine.

3. A method of claim 1, wherein the effective amount of the cytotoxic polyamine compound is from about 0.5 μM to about 50 mM.

4. A method of claim 1, wherein the effective amount of the cytotoxic polyamine compound is from about 1.0 μM to about 25 mM.

5. A method of claim 1, additionally comprising contacting the cells with an amount of a polyamine depleting agent selected from the group consisting of difluoromethylornithine and (2R,5R)-6-heptyne-2,5-diamine.

6. A method of claim 2, additionally comprising contacting the cells with an amount of a polyamine depleting agent selected from the group consisting of difluoromethylornithine and (2R,5R)-6-heptyne-2,5-diamine.

7. A method of claim 5, wherein the polyamine depleting agent comprises difluoromethylornithine.

8. A method of claim 6, wherein the polyamine depleting agent comprises difluoromethylornithine.

9. A method of claim 5, wherein the effective amount of the polyamine-depleting agent is from about 1 μM to about 1 mM.

10. A method of claim 1, wherein the effective amount of the polyamine depleting agent is from about 250 μM to about 0.5 mM.

11. A method of inhibiting the proliferation of prostate cancer cells in a human subject afflicted with prostate cancer comprising administering to the subject an effective proliferation inhibiting amount of a cytotoxic polyamine selected from the group consisting of 1-(4-aminobutyl) aziridine, ($N^1$-(3-aminopropyl)-1,4-butanediamine) aziridine and N,$N^1$-bis (3-aminopropyl)-1,4-butanediamine) aziridine effective to inhibit the proliferation of prostate cancer cells in a human subject.

12. A method of claim 11, wherein the cytotoxic polyamine compound comprises 1-(4-aminobutyl) aziridine.

13. A method of claim 11, wherein the effective amount of the cytotoxic polyamine compound is from about 0.5 μM to about 50 mM.

14. A method of claim 11, wherein the effective amount of the cytotoxic polyamine compound is from about 1.0 μM to about 25 mM.

15. A method of claim 11, additionally comprising contacting the subject with an amount of a polyamine depleting agent selected from the group consisting of difluoromethylornithine, and (2R,5R)-6-heptyne-2,5-diamine.

16. A method of claim 12, additionally comprising contacting with an amount of a polyamine selected from the group consisting of difluoromethylornithine, and (2R,5R)-6-heptyne-2,5-diamine.

17. A method of claim 15, wherein the polyamine depleting agent comprises difluoromethylornithine.

18. A method of claim 12, wherein the polyamine depleting agent comprises difluoromethylornithine.

19. A method of claim 11, wherein the effective amount of the polyamine-depleting agent is from about 0.5 μM to about 50 mM.

20. A method of claim 14, wherein the effective amount is from about 1.0 μM to about 25 mM.

21. A two component therapeutic composition useful to inhibit proliferation of a human prostate cancer cells which comprises separate first and second components, the first component comprising an effective prostate cancer cell proliferation inhibiting amount of a cytotoxic polyamine selected from the group consisting of 1-(4-aminobutyl) aziridine, (N-(3-aminopropyl)-1,4-butanediamine), and (N,$N^1$-bis (3-aminopropyl)-1,4-butanediamine) aziridine and the second component comprising an amount of a polyamine depleting agent selected from the group consisting of difluoromethylornithine, and (2R,5R)-6-heptyne-2,5-diamine.

22. A composition of claim 21, wherein the cytotoxic polyamine compound is 1-(4-aminobutyl) aziridine.

23. A composition of claim 22, wherein the effective amount of 1-(4-aminobutyl) aziridine is from about 0.5 μM to about 50 mM.

24. A composition of claim 22, wherein the effective amount of 1-(4-aminobutyl) aziridine is from about 1.0 μM to about 25 mM.

25. A composition of claim 21, wherein the polyamine-depleting agent is difluoromethylornithine.

26. A composition of claim 21, wherein the effective amount of the cytotoxic polyamine compound is from about 0.5 μM to about 50 mM.

27. A composition of claim 26, wherein the effective amount is from about 1.0 μM to about 25 mM.

28. A composition of claim 21, wherein the effective amount of the polyamine-depleting agent is from about 0.5 μM to about 50 mM.

29. A composition of claim 28, wherein the effective amount is from about 1.0 μM to about 25 mM.

* * * * *